(12) United States Patent
Okuda et al.

(10) Patent No.: US 8,355,130 B2
(45) Date of Patent: Jan. 15, 2013

(54) METHOD FOR EVALUATING WHITE COLOR SHIELDING DEGREE, METHOD FOR MANUFACTURING WHITE INK, SUPPORT APPARATUS FOR MANUFACTURING WHITE INK, AND METHOD FOR MANUFACTURING WHITE COLOR PRINTED MATERIAL

(75) Inventors: Ippei Okuda, Shiojiri (JP); Takayoshi Kagata, Shiojiri (JP); Tsuyoshi Sano, Shiojiri (JP)

(73) Assignee: Seiko Epson Corporation, Tokyo (JP)

( * ) Notice: Subject to any disclaimer, the term of this patent is extended or adjusted under 35 U.S.C. 154(b) by 320 days.

(21) Appl. No.: 12/832,496

(22) Filed: Jul. 8, 2010

(65) Prior Publication Data

US 2011/0007318 A1  Jan. 13, 2011

(30) Foreign Application Priority Data

Jul. 8, 2009  (JP) .................................. 2009-161350

(51) Int. Cl.
  *G01N 21/00* (2006.01)
(52) U.S. Cl. ....................................................... 356/433
(58) Field of Classification Search .................. None
  See application file for complete search history.

(56) References Cited

U.S. PATENT DOCUMENTS

| 2003/0149130 A1 | 8/2003 | Kondo |
| 2008/0081119 A1 | 4/2008 | Oyanagi et al. |
| 2009/0021526 A1* | 1/2009 | Chiang et al. ................. 345/605 |
| 2009/0046928 A1* | 2/2009 | Kwak et al. ................... 382/167 |

FOREIGN PATENT DOCUMENTS

| JP | 06-323911 A | 11/1994 |
| JP | 2003-182061 A | 7/2003 |
| JP | 2006-058087 A | 3/2006 |
| JP | 2007-161847 A | 6/2007 |
| JP | 2008-075067 A | 4/2008 |
| JP | 2008-087287 A | 4/2008 |
| JP | 2009-035672 A | 2/2009 |

* cited by examiner

*Primary Examiner* — Tu Nguyen
(74) *Attorney, Agent, or Firm* — Nutter McClennen & Fish LLP; John J. Penny, V

(57) ABSTRACT

A method for obtaining and evaluating a white color shielding degree of a white color printed material includes the steps of: measuring an L* value of the white color printed material; obtaining an integrated value of transmittance of the white color printed material in a visible light region; and obtaining the white color shielding degree from the L* value and the integrated value.

6 Claims, 8 Drawing Sheets

FIG. 4

TABLE 1

| | REFERENCE EXAMPLE 1 | REFERENCE EXAMPLE 2 | EXAMPLE 1-1 | EXAMPLE 2-1 | EXAMPLE 3-1 | EXAMPLE 4-1 | EXAMPLE 5 |
|---|---|---|---|---|---|---|---|
| TITANIUM DIOXIDE PARTICLES (SOLID COMPONENT) | — | 10 | 10 | 10 | 10 | 10 | — |
| HOLLOW RESIN PARTICLES (SOLID COMPONENT) | — | — | — | — | — | — | 10 |
| ACRYL STYRENE RESIN (SOLID COMPONENT) | — | — | 4 | — | — | — | — |
| URETHANE RESIN A (SOLID COMPONENT) | — | — | — | 4 | — | — | 4 |
| URETHANE RESIN B (SOLID COMPONENT) | — | — | — | — | 4 | — | — |
| URETHANE RESIN C (SOLID COMPONENT) | — | — | — | — | — | 4 | — |
| SURFACTANT | — | 1 | 1 | 1 | 1 | 1 | 1 |
| PROPYLENE GLYCOL | — | 2 | 2 | 2 | 2 | 2 | 2 |
| 1,2-HEXANEDIOL | — | 5 | 5 | 5 | 5 | 5 | 5 |
| 2-PYRROLIDONE | — | 2 | 2 | 2 | 2 | 2 | 2 |
| WATER | BALANCE | BALANCE | BALANCE | BALANCE | BALANCE | BALANCE | BALANCE |
| L* VALUE | — | 70.3 | 76.8 | 74.8 | 75.3 | 74.9 | 78.5 |
| INTEGRATED VALUE | 12136 | 1113.9 | 194.3 | 151.76 | 119.17 | 102.45 | 194.5 |
| LS VALUE | 0 | 4.7 | 60 | 64 | 86 | 96 | 69 |
| SHIELDING DEGREE (EVALUATION) | E | D | C | B | A | AA | B |

PERCENT BY MASS %

ACRYL STYRENE RESIN: "JOHNCRYL 62J" MANUFACTURED BY BASF
URETHANE RESIN A: "D6300" MANUFACTURED BY DAINICHISEIKA COLOR & CHEMICAL MFG. CO., LTD.
URETHANE RESIN B: "D6455" MANUFACTURED BY DAINICHISEIKA COLOR & CHEMICAL MFG. CO., LTD.
URETHANE RESIN C: "D2020" MANUFACTURED BY DAINICHISEIKA COLOR & CHEMICAL MFG. CO., LTD.

FIG. 5

TABLE 2

| | EXAMPLE 2-1 | EXAMPLE 2-2 | EXAMPLE 2-3 | EXAMPLE 2-4 |
|---|---|---|---|---|
| TITANIUM DIOXIDE PARTICLES (SOLID COMPONENT) | 10 | 10 | 10 | 10 |
| HOLLOW RESIN PARTICLES (SOLID COMPONENT) | — | — | — | — |
| ACRYL STYRENE RESIN (SOLID COMPONENT) | — | — | — | — |
| URETHANE RESIN A (SOLID COMPONENT) | 4 | — | — | — |
| URETHANE RESIN B (SOLID COMPONENT) | — | — | — | — |
| URETHANE RESIN C (SOLID COMPONENT) | — | — | — | — |
| W635 (SOLID COMPONENT) | | 4 | | |
| AQ515 (SOLID COMPONENT) | | | 4 | |
| W605 (SOLID COMPONENT) | | | | 4 |
| SURFACTANT | 1 | 1 | 1 | 1 |
| PROPYLENE GLYCOL | 2 | 2 | 2 | 2 |
| 1, 2-HEXANEDIOL | 5 | 5 | 5 | 5 |
| 2-PYRROLIDONE | 2 | 2 | 2 | 2 |
| WATER | BALANCE | BALANCE | BALANCE | BALANCE |
| L* VALUE | 74.8 | 74.6 | 75.9 | 74.2 |
| INTEGRATED VALUE | 151.76 | 117.92 | 151.49 | 143.34 |
| LS VALUE | 64 | 81 | 71 | 64 |
| SHIELDING DEGREE (EVALUATION) | B | B | B | B |

PERCENT BY MASS %

ACRYL STYRENE RESIN: "JOHNCRYL 62J" MANUFACTURED BY BASF
URETHANE RESIN A: "D6300" MANUFACTURED BY DAINICHISEIKA COLOR & CHEMICAL MFG. CO., LTD.
URETHANE RESIN B: "D6455" MANUFACTURED BY DAINICHISEIKA COLOR & CHEMICAL MFG. CO., LTD.
URETHANE RESIN C: "D2020" MANUFACTURED BY DAINICHISEIKA COLOR & CHEMICAL MFG. CO., LTD.

FIG. 6

TABLE 3

|  | EXAMPLE 3-1 | EXAMPLE 3-2 |
|---|---|---|
| TITANIUM DIOXIDE PARTICLES (SOLID COMPONENT) | 10 | 10 |
| HOLLOW RESIN PARTICLES (SOLID COMPONENT) | — | — |
| ACRYL STYRENE RESIN (SOLID COMPONENT) | — | — |
| URETHANE RESIN A (SOLID COMPONENT) | — | — |
| URETHANE RESIN B (SOLID COMPONENT) | 4 | — |
| URETHANE RESIN C (SOLID COMPONENT) | — | — |
| WS6021 (SOLID COMPONENT) | — | 4 |
| SURFACTANT | 1 | 1 |
| PROPYLENE GLYCOL | 2 | 2 |
| 1, 2-HEXANEDIOL | 5 | 5 |
| 2-PYRROLIDONE | 2 | 2 |
| WATER | BALANCE | BALANCE |
| L* VALUE | 75.3 | 74.7 |
| INTEGRATED VALUE | 119.27 | 113.28 |
| LS VALUE | 86 | 85 |
| SHIELDING DEGREE (EVALUATION) | A | A |

PERCENT BY MASS %

ACRYL STYRENE RESIN: "JOHNCRYL 62J" MANUFACTURED BY BASF
URETHANE RESIN A: "D6300" MANUFACTURED BY DAINICHISEIKA COLOR & CHEMICAL MFG. CO., LTD.
URETHANE RESIN B: "D6455" MANUFACTURED BY DAINICHISEIKA COLOR & CHEMICAL MFG. CO., LTD.
URETHANE RESIN C: "D2020" MANUFACTURED BY DAINICHISEIKA COLOR & CHEMICAL MFG. CO., LTD.

FIG. 7

TABLE 4

| | EXAMPLE 4-1 | EXAMPLE 4-2 | EXAMPLE 4-3 |
|---|---|---|---|
| TITANIUM DIOXIDE PARTICLES (SOLID COMPONENT) | 10 | 10 | 10 |
| HOLLOW RESIN PARTICLES (SOLID COMPONENT) | — | — | — |
| ACRYL STYRENE RESIN (SOLID COMPONENT) | — | — | — |
| URETHANE RESIN A (SOLID COMPONENT) | — | — | — |
| URETHANE RESIN B (SOLID COMPONENT) | — | — | — |
| URETHANE RESIN C (SOLID COMPONENT) | 4 | — | — |
| D4200 (SOLID COMPONENT) | | 4 | |
| WS5000 (SOLID COMPONENT) | | | 4 |
| SURFACTANT | 1 | 1 | 1 |
| PROPYLENE GLYCOL | 2 | 2 | 2 |
| 1, 2-HEXANEDIOL | 5 | 5 | 5 |
| 2-PYRROLIDONE | 2 | 2 | 2 |
| WATER | BALANCE | BALANCE | BALANCE |
| L* VALUE | 74.9 | 74.2 | 74.8 |
| INTEGRATED VALUE | 102.45 | 104.19 | 100.88 |
| LS VALUE | 96 | 88 | 97 |
| SHIELDING DEGREE (EVALUATION) | AA | AA | AA |

PERCENT BY MASS %

ACRYL STYRENE RESIN: "JOHNCRYL 62J" MANUFACTURED BY BASF
URETHANE RESIN A: "D6300" MANUFACTURED BY DAINICHISEIKA COLOR & CHEMICAL MFG. CO., LTD.
URETHANE RESIN B: "D6455" MANUFACTURED BY DAINICHISEIKA COLOR & CHEMICAL MFG. CO., LTD.
URETHANE RESIN C: "D2020" MANUFACTURED BY DAINICHISEIKA COLOR & CHEMICAL MFG. CO., LTD.

FIG. 8

| RESIN | COMPOSITION | RESIN | COMPOSITION |
|---|---|---|---|
| JOHNCRYL 62J | ACRYL STYRENE RESIN | D6455 | CARBONATE-BASED URETHANE RESIN |
| W635 | CARBONATE-BASED URETHANE RESIN | D2020 | ETHER-BASED URETHANE RESIN |
| D6300 | CARBONATE-BASED URETHANE RESIN | D4200 | ETHER-BASED URETHANE RESIN + CARBONATE-BASED URETHANE RESIN |
| W605 | ESTER-BASED URETHANE RESIN | WS6021 | ETHER-BASED URETHANE RESIN |
| AQ515 | POLYETHYLENE RESIN | WS5000 | ESTER-BASED URETHANE RESIN |

FIG. 9

| COLOR MATERIAL | RESIN | L* VALUE | INTEGRATED VALUE | APPEARANCE | LS VALUE |
|---|---|---|---|---|---|
| – | PET | – | 12136 | E | 0 |
| TITANIUM DIOXIDE | – | 70.3 | 1113.9 | D | 6 |
| | JOHNCRYL 62J | 76.8 | 194.3 | C | 60 |
| | W635 | 74.6 | 117.92 | B | 81 |
| | AQ515 | 75.9 | 151.49 | B | 71 |
| | D6300 | 74.8 | 151.76 | B | 64 |
| | W605 | 74.2 | 143.34 | B | 64 |
| | WS6021 | 74.7 | 113.28 | A | 85 |
| | D6455 | 75.3 | 119.17 | A | 86 |
| | D2020 | 74.9 | 102.45 | AA | 96 |
| | D4200 | 74.2 | 104.19 | AA | 88 |
| | WS5000 | 74.8 | 100.88 | AA | 97 |
| HOLLOW RESIN | D6455 | 78.5 | 194.5 | B | 69 |

METHOD FOR EVALUATING WHITE COLOR SHIELDING DEGREE, METHOD FOR MANUFACTURING WHITE INK, SUPPORT APPARATUS FOR MANUFACTURING WHITE INK, AND METHOD FOR MANUFACTURING WHITE COLOR PRINTED MATERIAL

BACKGROUND

1. Technical Field

The present invention relates to a white color printed material formed by using a white ink, and more particularly relates to, besides providing a novel method for evaluating a white color shielding degree of a white color printed material printed on a transparent substrate having no ink absorbing properties, a method for manufacturing a white ink based on the white color shielding degree, a support apparatus for manufacturing a white ink, and a method for manufacturing a white color printed material.

2. Related Art

An ink jet recording method is able to record a highly fine image by a relatively simple device and has been rapidly developed in various fields. In addition, the ink jet recording method has been used in many various fields, and in accordance with each application, appropriate recording medium and/or ink is used.

In addition, as the index for evaluating a white color printed material formed by using a white ink, an L* value (degree of lightness by reflected light) has been commonly used.

In addition, heretofore, the visibility has been improved by using a white color material (pigment), such as titanium oxide. However, since the thickness of an ink layer is increased at a dot portion of a color image, curing by radiation of active energy rays through a white color layer cannot be sufficiently carried out, and hence, because of curing defects of a color ink layer, for example, color bleeding is generated.

As for a white ink, an ink jet recording method has been known which has superior visibility and gradation reproduction characteristics even when a transparent recording medium or a recording medium having low lightness is used (see JP-A-2003-182061).

The following has been disclosed in JP-A-2003-182061.

When an image is viewed on a recording medium, a white image is formed with a white ink on a recording medium using an ink jet printer having gradation reproduction means, and a color image having gradation characteristics is formed as a normal image on the white image using a color ink.

In addition, when an image is viewed through a recording medium, a color image having gradation characteristics is first formed on the recording medium as a reversed image, and a white image is then formed thereon using a white ink.

In the case described above, in order to obtain superior color development and gradation characteristics of a color image, a white ink layer having a transmission density of 0.15 or more and an L* value of 65 or more is preferable.

More preferably, the transmission density is 0.2 or more, and the L* value is 70 or more. Accordingly, when the values are lower than those described above, or when no white ink layer is present, the contrast between a recording medium and a color image cannot be obtained, and as a result, the visibility may be degraded, or in particular, since the gradation characteristics are not obtained in a low density region, degradation of image quality may occur in some cases. Although the upper limit is not particularly defined, as a level of high density in view of ink manufacturing, the transmission density is 0.5 or less, and the L* value is 100 or less.

According to the invention disclosed in JP-A-2003-182061, it has been disclosed that in order to obtain superior color development and gradation characteristics of a color image, the transmission density and the L* value are preferably set to 0.15 or more and 65 or more and more preferably set to 0.2 or more and 70 or more, respectively. Hence, in the above invention, higher transmission density and L* value are both particularly specified.

The white ink disclosed in JP-A-2003-182061 shows the restriction to obtain superior color development and gradation characteristics of a color image.

The inventor of the invention discovered that although as a related index for evaluating a white color printed material, the L* value (degree of lightness by reflected light) is generally used, shielding characteristics (shielding degrees) of white color printed materials are differently viewed in many cases even if the L* values thereof are equal to each other, and that this difference is caused by the type and the content of resin used for a white ink.

SUMMARY

An advantage of some aspects of the invention is to provide a novel method for evaluating white color shielding properties using a newly defined "white color shielding degree" which will be described below, a method for manufacturing a white ink based on the white color shielding degree, a support apparatus for manufacturing a white ink, and a method for manufacturing a white color printed material. Based on the knowledge that even if the L* values of white color printed materials are equal to each other, shielding properties thereof are differently viewed in many cases, the above "white color shielding degree" is newly defined as the definition of the whiteness of a white color printed material and is obtained from $[(L^* \text{ value}-\alpha)/\text{integrated value}]\times 1{,}000$ (hereinafter referred to as "lightness shielding (LS) value") which is a value relating to both "L* value" and "integrated value of transmittance in a visible light region".

A method for evaluating a white color shielding degree according to one aspect of the invention is a method for obtaining and evaluating a white color shielding degree of a white color printed material, the method including: measuring an L* value of the white color printed material; obtaining an integrated value of transmittance of the white color printed material in a visible light region; and obtaining the white color shielding degree from the L* value and the integrated value.

In addition, the integrated value of transmittance is an integrated value of transmittance in a wavelength of 380 to 700 nm.

In addition, the white color printed material is a printed material in which recording is performed on a transparent medium with a white ink, and the white color shielding degree (LS value) is represented by $[(L^* \text{ value}-\alpha)/\text{integrated value}]\times 1{,}000$.

The $\alpha$ is a predetermined value of 60 to 70 to increase influence of the change in L* value in a white color region and is preferably "65"; however, the $\alpha$ may not be always limited thereto, and another value may also be used.

In addition, depending on whether the white color shielding degree (LS value) is not less than a predetermined value or not, the white color shielding degree (LS value) is evaluated at one of levels represented by AA, A, B, C, and D.

In addition, the white ink includes at least a color material and a fixing resin. Furthermore, the color material includes titanium dioxide particles or hollow resin particles.

A method for manufacturing a white ink according to another aspect of the invention is a method for manufacturing an ink using a support apparatus for manufacturing a white ink, the support apparatus including: means for inputting the type of color material; means for setting a white color shielding degree; a memory portion storing a table which defines the relationship between the type of fixing resin corresponding to the color material and the white color shielding degree; and an arithmetic processing portion. The method for manufacturing a white ink described above includes: determining the type of color material; setting a desired white color shielding degree; and in accordance with the set value of the white color shielding degree, determining the type of fixing resin with reference to the table stored in advance.

In addition, when the white color shielding degree of a white color printed material formed using a manufactured white ink is measured, the content of the table is renewed thereby.

A support apparatus for manufacturing a white ink according to another aspect of the invention is a support apparatus for manufacturing a white ink which includes at least a color material and a fixing resin, and the support apparatus includes: means for inputting the type of color material to be used; means for setting a desired white color shielding degree; a memory portion storing a table which defines the relationship in accordance with each color material between the type of fixing resin and a white color shielding degree; and an arithmetic processing portion determining the type of fixing resin in accordance with the set value of the white color shielding degree with reference to the table.

A method for manufacturing a white color printed material according to another aspect of the invention is a method for manufacturing a white color printed material which is printed at a value of $[(L^* \text{ value} - \alpha)/\text{integrated value}] \times 1{,}000$, which is predetermined as a white color shielding degree (LS value), using a white ink manufactured by the method for manufacturing a white ink described above.

The $\alpha$ is a predetermined value of 60 to 70 to increase influence of the change in $L^*$ value in a white color region and is preferably "65"; however, the value may not be always limited thereto, and another value may also be used.

According to the invention, as a novel definition of shielding properties of a white color printed material, the "white color shielding degree" represented by "$[(L^* \text{ value} - \alpha)/\text{integrated value}] \times 1{,}000$" is defined which relates to both the "$L^*$ value" and the "integrated value of transmittance in a visible light region", and in addition, a novel method for evaluating white color shielding properties using the defined white color shielding degree is not only realized, but a method for manufacturing a white ink based on the white color shielding degree, a support apparatus for manufacturing a white ink, and a method for manufacturing a white color printed material can also be realized.

BRIEF DESCRIPTION OF THE DRAWINGS

The invention will be described with reference to the accompanying drawings, wherein like numbers reference like elements.

FIG. 4 is Table 1 showing representative examples in which the white color shielding degrees (LS values) are evaluated at levels AA, A, B, C, D, and E.

FIG. 5 is Table 2 showing other examples in which the white color shielding degrees are evaluated at the level B which is the same as the shielding degree (evaluation) of Example 2-1 of Table 4.

FIG. 6 is Table 3 showing another example in which the white color shielding degree is evaluated at the level A which is the same as the shielding degree (evaluation) of Example 3-1 of Table 4.

FIG. 7 is Table 4 showing other examples in which the white color shielding degrees are evaluated at the level AA which is the same as the shielding degree (evaluation) of Example 4-1 of Table 4.

FIG. 8 shows a table in which the names of resins and compositions thereof are shown.

FIG. 9 shows one example of a table in which the relationship among the type of fixing resin, an $L^*$ value, an integrated value, appearance (level), and a white color shielding degree (LS value) is shown which is obtained when titanium dioxide or a hollow resin is used as a color material.

DESCRIPTION OF EXEMPLARY EMBODIMENTS

Figure 1:
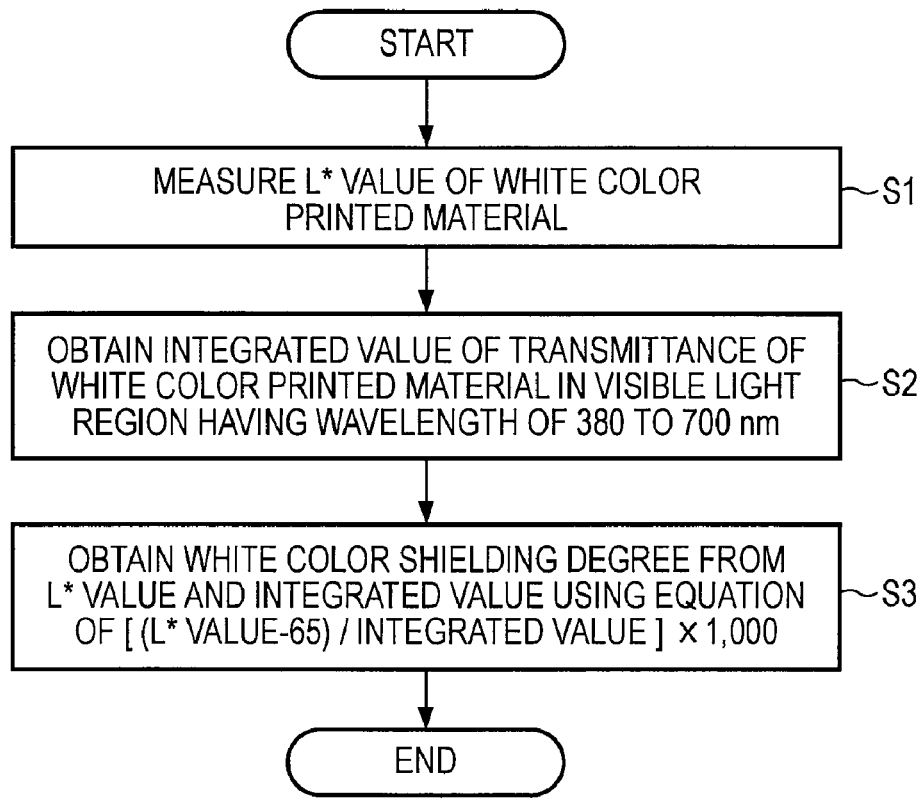
FIG. 1 is a flowchart illustrating basic operations of a method for obtaining and evaluating a white color shielding degree of a white color printed material of the invention.

Embodiments for carrying out the invention will be described below.

A method for evaluating a white color shielding degree according to an embodiment of the invention includes: measuring an $L^*$ value of a white color printed material; obtaining an integrated value of transmittance of the white color printed material in a visible light region; and obtaining the white color shielding degree from the $L^*$ value and the integrated value, so that the white color shielding degree of the white color printed material is obtained and evaluated.

In the invention, the "white color shielding degree" is the degree of light of a fluorescent lamp viewed by an observer, the degree being obtained when a printed material in which a white ink is printed on a transparent medium is viewed through light emitted from the fluorescent lamp disposed therebehind, and is evaluated, for example, at one of 6 stages of AA, A, B, C, D, and E.

A method for manufacturing a white ink according to an embodiment of the invention includes: determining the type of color material; setting a desired white color shielding degree; and in accordance with the set value of the white color shielding degree, determining the type of fixing resin with reference to a table stored in advance in accordance with the color material, the table defining the relationship between the fixing resin and the white color shielding degree.

A support apparatus for manufacturing a white ink according to an embodiment of the invention includes: means for inputting the type of color material to be used; means for setting a desired white color shielding degree; a table which defines the relationship between the type of fixing resin and a white color shielding degree; and means for determining the type of fixing resin with reference to the table in accordance with the set value of the desired white color shielding degree.

1. White Ink Composition
1.1 Color Material

A white ink composition according to an embodiment of the invention preferably includes, for example, a metal compound or hollow resin particles as a white color material.

As the metal compound of the invention, any compound containing a metal element may be used as long as it can be used as a pigment, and for example, metal oxides which have been used as a white pigment, barium sulfate, and calcium carbonate may be mentioned. Although the metal oxides are not particularly limited, for example, titanium dioxide, zinc oxide, silica, alumina, and magnesium oxide may be mentioned. Among those mentioned above, titanium dioxide and alumina are preferable as the metal compound of the invention.

The content of the above metal compound is, with respect to the total mass of the white ink composition, preferably 1.0 to 20.0 percent by mass and more preferably 5.0 to 10.0 percent by mass. When the content of the metal compound is more than 20.0 percent by mass, for example, an ink jet recording head may be clogged, so that the reliability is degraded in some cases. On the other hand, when the content is less than 1.0 percent by mass, the color density, such as the degree of whiteness, tends to be insufficient.

The average particle diameter (outside diameter) of the metal compound is preferably 30 to 600 nm and more preferably 200 to 400 nm. When the outside diameter is more than 600 nm, for example, the particles may precipitate to disturb the dispersion stability thereof, and clogging of an ink jet recording head may occur, so that the reliability is degraded in some cases. On the other hand, when the outside diameter is less than 30 nm, the color density, such as the degree of whiteness, tends to be insufficient.

The average particle diameter of the metal compound may be measured by a particle distribution measurement device using a laser diffraction scattering method as a measurement principle. As the laser diffraction particle distribution measurement device, for example, a particle distribution measurement device (for example, "Microtrack UPA" manufactured by Nikkiso Co., Ltd.) using a dynamic light scattering method as a measurement principle may be used.

As the hollow resin particles of the invention, particles each having a cavity inside and an outer shell formed of a liquid permeable resin are preferable. By the structure as described above, when the hollow resin particles are present in an aqueous ink composition, the inside cavities of the particles are filled with an aqueous medium. Since the particles filled with an aqueous medium have a specific gravity approximately equivalent to that of an aqueous medium outside the particles, the particles can maintain the dispersion stability in the aqueous ink composition without precipitating. Accordingly, the storage stability and the ejection stability of the white ink composition can be improved.

In addition, when the white ink composition including hollow resin particles is ejected on paper or another recording medium, an aqueous medium inside the particles evaporates in drying, so that their cavities are filled with air. Since containing air inside, the particles each have a resin layer and an air layer having a different refractive index therefrom, and incident light is effectively scattered thereby, so that a white color can be obtained. Incidentally, when resin layers that form hollow resin particles are colored while retaining the light transparency, a color different from white can be obtained.

The hollow resin particles used in the invention are not particularly limited, and known particles may be used. For example, hollow resin particles disclosed, for example, in U.S. Pat. No. 4,880,465, Japanese Patent No. 3,562,754 may be preferably used.

The average particle diameter (outside diameter) of the hollow resin particles is preferably 0.2 to 1.0 μm and more preferably 0.4 to 0.8 μm. When the outside diameter is more than 1.0 μm, for example, the particles may precipitate to disturb the dispersion stability thereof, and clogging of an ink jet recording head may occur, so that the reliability is degraded in some cases. On the other hand, when the outside diameter is less than 0.2 μm, the color density, such as the degree of whiteness, tends to be insufficient. In addition, an appropriate inside diameter is approximately 0.1 to 0.8 μm.

The average particle diameter of the hollow resin particles may be measured by a particle distribution measurement device using a laser diffraction scattering method as a measurement principle. As the laser diffraction particle distribution measurement device, for example, a particle distribution measurement device (for example, "Microtrack UPA" manufactured by Nikkiso Co., Ltd.) using a dynamic light scattering method as a measurement principle may be used.

The content (solid component) of the hollow resin particles is, with respect to the total mass of the white ink composition, preferably 5 to 20 percent by mass and more preferably 8 to 15 percent by mass. When the content (solid component) of the hollow resin particles is more than 20 percent by mass, for example, clogging of an ink jet recording head may occur, so that the reliability is degraded in some cases. On the other hand, when the content is less than 5 percent by mass, the color density, such as the degree of whiteness, tends to be insufficient.

A method for preparing the hollow resin particles is not particularly limited, and a known method may be used. As the method for preparing hollow resin particles, for example, a so-called emulsion polymerization method may be used in which a vinyl monomer, a surfactant, a polymerization initiator, and an aqueous dispersion medium are heated and stirred in a nitrogen atmosphere to form a hollow resin-particle emulsion.

As the vinyl monomer, a nonionic monoethylene unsaturated monomer may be mentioned, and for example, styrene, vinyltoluene, ethylene, vinyl acetate, vinyl chloride, vinylidene chloride, acrylonitrile, (meth)acrylamide, and a (meth)acrylate may be mentioned. As the (meth)acrylate, for example, methyl acrylate, methyl methacrylate, ethyl(meth)acrylate, butyl(meth)acrylate, 2-hydroxyethyl methacrylate, 2-ethylhexyl(meth)acrylate, benzyl(meth)acrylate, lauryl (meth)acrylate, oleyl(meth)acrylate, palmityl(meth)acrylate, and stearyl(meth)acrylate may be mentioned.

In addition, as the vinyl monomer, a difunctional vinyl monomer may also be used. As the difunctional vinyl monomer, for example, divinylbenzene, allyl methacrylate, ethylene glycol dimethacrylate, 1,3-butanediol dimethacrylate, diethylene glycol dimethacrylate, and trimethylolpropane trimethacrylate may be mentioned. In addition, when the above monofunctional vinyl monomer and the above difunctional vinyl monomer are copolymerized to form a highly cross-linked state, hollow resin particles can be obtained that have various features, such as heat resistance, solvent resistance, and solvent dispersibility, as well as light scattering properties.

As the surfactant, any surfactant may be used as long as it forms molecular aggregates, such as micelles, in water, and for example, an anionic surfactant, a nonionic surfactant, a cationic surfactant, and an amphoteric surfactant may be mentioned.

As the polymerization initiator, a known water-soluble compound may be used, and for example, hydrogen peroxide and potassium persulfate may be mentioned.

As the aqueous dispersion medium, for example, water and water containing a hydrophilic organic solvent may be mentioned.

1.2 Fixing Resin

The white ink composition according to the embodiment of the invention preferably includes a fixing resin for fixing a color material.

As the fixing resin, any resin may be used as long as it is a transparent resin, and for example, an acryl styrene resin, a polyurethane resin, an acrylic resin, a styrene resin, a polyethylene resin, or a wax may be mentioned. Among those mentioned above, in order to obtain a higher white color shielding degree, a polyurethane resin is preferable, and a carbonate-based or an ether-based aliphatic urethane resin is particularly preferable.

As the polyurethane resin of the invention, either an emulsion type in which polyurethane resin particles are dispersed in a solvent or a solution type in which polyurethane resin particles are dissolved in a solvent may be used. In addition, the emulsion type may be classified in accordance with its emulsification method into a forced emulsification type and a self-emulsification type, and although both types may be used in this invention, a self-emulsification type is preferably used. Since a self-emulsification type dispersion is superior in film formation properties and moisture resistance to a forced emulsification type dispersion.

When the above emulsion type is used as the polyurethane resin, the average particle diameter thereof is preferably 50 to 200 nm and more preferably 60 to 200 nm. When the average particle diameter of the polyurethane resin is in the above range, polyurethane resin particles can be uniformly dispersed in the white ink composition.

The content (solid component) of the polyurethane resin is, with respect to the total mass of the white ink composition, preferably 0.5 to 10 percent by mass and more preferably 0.5 to 5 percent by mass. When the content of the polyurethane resin is more than 10 percent by mass, the reliability (clogging resistance, ejection stability, and the like) may be degraded, and appropriate properties (such as viscosity) as the ink may not be obtained in some cases. On the other hand, when the content is less than 0.5 percent by mass, the fixability of ink on a recording medium is not superior, and an image having superior rub-off resistance cannot be formed.

1.3 Permeable Organic Solvent

The white ink composition according to the embodiment of the invention preferably includes at least one selected from alkanediols and glycol ethers. Alkanediols and glycol ethers are each able to improve the wettability to a recording surface of a recording medium or the like and also to improve the permeability of ink.

As the alkanediols, 1,2-alkanediols having 4 to 8 carbon atoms, such as 1,2-butanediol, 1,2-pentanediol, 1,2-hexanediol, 1,2-heptanediol, and 1,2-octanediol, are preferably used. Among those mentioned above, 1,2-hexanediol, 1,2-heptanediol, and 1,2-octanediol, which have 6 to 8 carbon atoms, are more preferable since having significantly high permeability to a recording medium.

As the glycol ethers, for example, there may be mentioned lower alkyl ethers of polyalcohols, such as ethylene glycol monomethyl ether, ethylene glycol monoethyl ether, ethylene glycol monobutyl ether, diethylene glycol monomethyl ether, diethylene glycol monoethyl ether, diethylene glycol monobutyl ether, dipropylene glycol monomethyl ether, dipropylene glycol monoethyl ether, triethylene glycol monomethyl ether, triethylene glycol monobutyl ether, and tripropylene glycol monomethyl ether. Among those mentioned above, superior recording quality can be obtained when triethylene glycol monobutyl ether is used.

The content of at least one selected from those alkanediols and glycol ethers is, with respect to the total mass of the white ink composition, preferably 1 to 20 percent by mass and more preferably 1 to 10 percent by mass.

1.4 Surfactant

The white ink composition according to the embodiment of the invention preferably includes an acetylene glycol-based surfactant or a polysiloxane-based surfactant. An acetylene glycol-based surfactant and a polysiloxane-based surfactant are each able to improve the wettability to a recording surface of a recording medium or the like and also to improve the permeability of ink.

As the acetylene glycol-based surfactant, for example, 2,4,7,9-tetramethyl-5-decyne-4,7-diol, 3,6-dimethyl-4-octyne-3,6-diol, 3,5-dimethyl-1-hexyne-3-ol, or 2,4-dimethyl-5-hexyne-3-ol may be mentioned. In addition, commercially available acetylene glycol-based surfactants may also be used, and for example, Olfine E1010, STG, and Y (manufactured by Nissin Chemical Industry Co., Ltd.) and Surfynol 104, 82, 465, 485, and TG (manufactured by Air Products and Chemicals Inc.) may be mentioned.

As the polysiloxane-based surfactant, a commercially available product may be used, and for example, BYK-347 and BYK-348 (manufactured by BYK Japan KK) may be mentioned.

Furthermore, the white ink composition according to the embodiment of the invention may also include another surfactant, such as an anionic surfactant, a nonionic surfactant, or an amphoteric surfactant.

The content of the above surfactant is, with respect to the total mass of the white ink composition, preferably 0.01 to 5 percent by mass and more preferably 0.1 to 0.5 percent by mass.

1.5 Polyalcohol

The white ink composition according to the embodiment of the invention preferably includes a polyalcohol. When the white ink composition of this invention is applied to an ink jet recording apparatus, a polyalcohol can suppress ink from being dried and can prevent clogging of an ink jet recording head portion caused by ink.

As the polyalcohol, for example, there may be mentioned ethylene glycol, diethylene glycol, triethylene glycol, polyethylene glycol, polypropylene glycol, propylene glycol, butylene glycol, 1,2,6-hexanetriol, thioglycol, hexylene glycol, glycerin, trimethylolethane, or trimethylolpropane.

The content of the polyalcohol is, with respect to the total mass of the white ink composition, preferably 0.1 to 30 percent by mass and more preferably 0.5 to 20 percent by mass.

1.6 Tertiary Amine

The white ink composition according to the embodiment of the invention preferably includes a tertiary amine. A tertiary amine functions as a pH adjuster and can easily adjust pH of the white ink composition.

As the tertiary amine, for example, triethanolamine may be mentioned. The content of the tertiary amine is, with respect to the total mass of the white ink composition, preferably 0.01 to 10 percent by mass and more preferably 0.1 to 2 percent by mass.

1.7 Solvent and Additives

The white ink composition according to the embodiment of the invention includes water as a common solvent. As water, purified water or ultrapure water, such as ion exchanged water, ultrafiltration water, reverse osmosis water, or distilled water, is preferably used. In particular, sterilized water obtained by treating the water mentioned above by ultraviolet radiation or by addition of hydrogen peroxide is preferably used since the generation of fungi and/or bacteria can be suppressed for a long period of time.

Whenever necessary, the white ink composition according to the embodiment of the invention may further include additives, that is, a fixing agent such as water-soluble rosin, a fungicide/antiseptic such as sodium benzoate, an antioxidant/UV absorber such as allophanates, a chelating agent, an oxygen absorber, and the like. The additives may be used alone and, of course, at least two thereof may be used in combination.

1.8 Preparation Method

The white ink composition according to the embodiment of the invention may be prepared using a known apparatus, such as a ball mill, a sand mill, an attritor, a basket mill, or a roll mill, in a manner similar to that for a related pigment ink. For preparation, coarse and large particles are preferably removed using a membrane filter, a mesh filter, or the like.

When the white ink composition according to the embodiment of the invention is applied on various recording media, white color images can be formed. As the recording media, for example, paper, heavy paper, fiber product, sheet or film, plastic, glass, and ceramic may be mentioned.

Application of the white ink composition according to the embodiment of the invention is not particularly limited, and this white ink composition may be applied to various types of ink jet recording systems. As the ink jet recording systems, for example, a thermal jet type ink jet, a piezoelectric type ink jet, a continuous ink jet, a roller application, and a spray application system may be mentioned.

After white inks are manufactured in combination of the above materials forming the ink composition, when the white color shielding degrees are measured, and table contents shown in FIG. 9 are renewed and are further enriched, a white ink having a desired white color shielding degree can be manufactured by using various materials.

EXAMPLES

Hereinafter, with reference to a flowchart shown in FIG. 1, there will be described basic operations of a method for obtaining and evaluating the white color shielding degree of a white color printed material according to one example of the embodiment.

The L*value of a white color printed material printed with a white ink is measured (Step S1).

The integrated value of transmittance of the white color printed material in a visible light region is obtained (Step S2).

The white color shielding degree is obtained from the L*value and the integrated value obtained in Steps S1 and S2, respectively (Step S3).

For measurement of the L* value, a commercially available color measurement apparatus, such as Gretag Macbeth Spectroscan and Spectrolino (manufactured by X-Rite Inc.), in which black was the base, was used.

For white color printing, the white ink composition described above was filled in a violet chamber of an exclusive cartridge of an ink jet printer ("PX-G930" manufactured by Seiko Epson Corp.). The ink cartridge thus formed was fitted in a printer, and printing test was performed.

Next, output was performed on Lumilar S-10-100 μm (manufactured by Toray Industries Inc.) at a resolution of 1,440×720 dpi.

In this specification, "duty" indicates the value calculated from the following equation.

$$\text{Duty (\%)} = [\text{actual number of printed dots}/(\text{vertical resolution} \times \text{horizontal resolution})] \times 100$$

(In the equation, the "actual number of printed dots" indicates the actual number of printed dots per unit area, and the "vertical resolution" and the "horizontal resolution" each indicate the resolution per unit area. The term of "100% duty" indicates the maximum ink mass of single color per one pixel.)

In addition, the integrated value of transmittance of a white color printed material sample is the integrated value of transmittance in a visible light region (for example, 380 to 700 nm). Although in this example, the above predetermined wavelength range was used, another predetermined wavelength range in the visible light region may also be used, and in this case, the correspondence between the LS value and the criterion level may be appropriately changed from that of this example.

In the invention, the integrated value of transmittance is obtained by the following method.

Light transmitted through the white color printed material sample is measured by a spectral photometer with an interval of 1 nm in the visible light region (380 to 700 nm in the invention), and the values thus measured are each output as a value in the range of 0 to 100 (unit: %).

When the values thus measured are integrated, the integrated value of transmittance (hereinafter simply referred to as the "integrated value") is obtained.

The integrated value thus obtained is a value in the range of 0 to 32,000, the complete shielding is represented by 0, and the complete transmission is represented by 32,000.

Although the above measurement is performed using a spectral photometer, instead of that, the reflectance may be measured by reflection mode measurement.

An equation to obtain the white color shielding degree from the L*value and the integrated value is as follows.

$$\text{White color shielding degree (LS value)} = [(L^* \text{ value} - \alpha)/\text{integrated value}] \times 1,000$$

In this equation, the reason $\alpha$ is subtracted from the L* value is to increase the influence of the change in L* value in a white color region, and the $\alpha$ is a predetermined value of 60 to 70 and is preferably "65"; however, the $\alpha$ must not be always limited thereto, and another value may also be used.

In this embodiment, the white color shielding degree (LS value) obtained in Step S3 is evaluated depending on whether the LS value is not less than a predetermined value or not.

That is, a plurality of levels (AA, A, B, C, D, and E) corresponding to results of sensory evaluation performed by an observer's visual inspection is set, and the numerical value of the white color shielding degree corresponding to each level is set based on actual measurement.

The criteria (degrees) of the above levels (AA, A, B, C, D, and E) are as follows.

White color shielding degree E: when a white color printed material is viewed through light emitted from a fluorescent lamp disposed therebehind, instead of the white color printed material, the light emitted from the fluorescent lamp is completely viewed.

White color shielding degree D: when a white color printed material is viewed through light emitted from a fluorescent lamp disposed therebehind, although the white color printed material is viewed, the light from the fluorescent lamp is clearly viewed.

White color shielding degree C.: when a white color printed material is viewed through light emitted from a fluorescent lamp disposed therebehind, although the light from the fluorescent lamp is clearly viewed, it is slightly cloudy.

White color shielding degree B: when a white color printed material is viewed through light emitted from a fluorescent lamp disposed therebehind, although the light from the fluorescent lamp is viewed, it is considerably cloudy.

White color shielding degree A: when a white color printed material is viewed through light emitted from a fluorescent lamp disposed therebehind, the light from the fluorescent lamp is hardly viewed.

White color shielding degree AA: when a white color printed material is viewed through light emitted from a fluorescent lamp disposed therebehind, the light from the fluorescent lamp is not viewed at all.

In this specification, the thresholds of the levels (AA, A, B, C, D, and E) of the white color shielding degree (LS value) are described as follows; however, the numerical values are not always limited thereto. In addition, the number of levels corresponding to the results of the sensory evaluation performed by an observer's visual inspection are not always limited to the above 6 levels.

White color shielding degree E indicates a transparent medium (not white color printed material).

White color shielding degree D indicates a white color printed material having an LS value of more than 0 to less than 54.

White color shielding degree C. indicates a white color printed material having an LS value of 54 or more.

White color shielding degree B indicates a white color printed material having an LS value of 64 or more.

White color shielding degree A indicates a white color printed material having an LS value of 82 or more.

White color shielding degree AA indicates a white color printed material having an LS value of 87 or more.

Next, an embodiment of a method for manufacturing a white ink composition of the invention will be described, the white ink composition at least including a color material and a fixing resin.

A method for manufacturing a white ink composition of the invention is a method for manufacturing an ink which uses a support apparatus for manufacturing a white ink composition, the support apparatus including: means for inputting the type of color material; means for setting a white color shielding degree; a memory portion storing a table which defines the relationship between the type of fixing resin corresponding to the color material and the white color shielding degree; and an arithmetic processing portion, and the method includes the steps of: determining the type of color material; setting a desired white color shielding degree, and in accordance with the set value of the white color shielding degree, determining the type of fixing resin with reference to the table stored in advance which defines the relationship between the type of fixing resin corresponding to the color material and the white color shielding degree.

Next, an embodiment of a support apparatus for manufacturing a white ink composition of the invention will be described with reference to FIG. 2.

Figure 2:
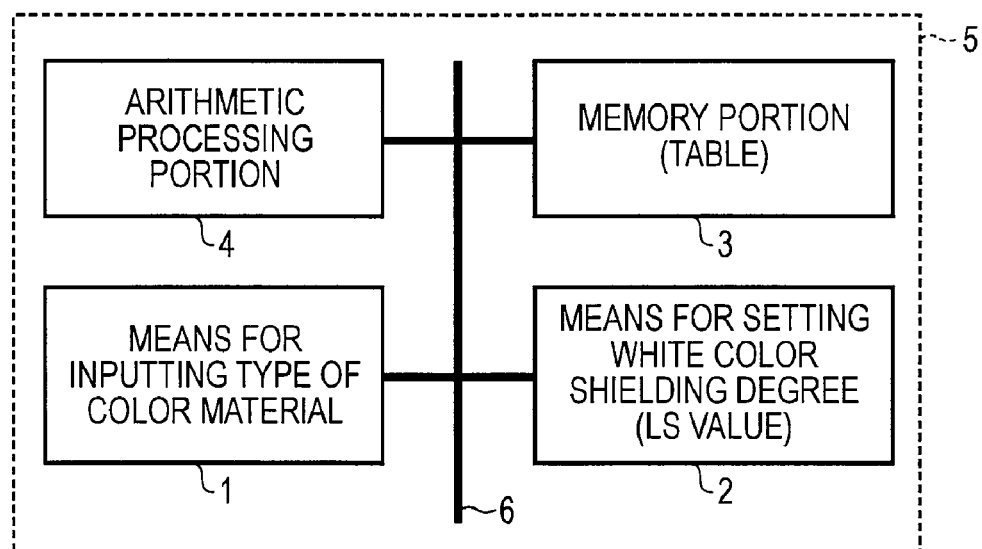
FIG. 2 is a view showing the structure of a support apparatus for manufacturing a white ink composition of the invention.

FIG. 2 shows the structure of the support apparatus for manufacturing a white ink composition of the invention.

In FIG. 2, reference numeral 1 indicates means for inputting the type of color material, reference numeral 2 indicates means for setting a white color shielding degree (LS value), reference numeral 3 indicates a memory portion storing a table which defines the relationship between the type of fixing resin corresponding to the color material and the white color shielding degree, reference numeral 4 indicates an arithmetic processing portion, and these four elements collectively form a support apparatus 5 for manufacturing a white ink composition.

The means for inputting the type of color material, the means for setting a white color shielding degree (LS value), and the memory portion are connected to the arithmetic processing portion through an internal bus 6.

The usage of the support apparatus 5 is as follows. That is, when the composition of ink is designed based on the white color shielding degree to manufacture a white ink, the following are performed.

The type of desired color material is determined and is input from the means 1 for inputting the type of color material.

A desired white color shielding degree is determined and is input from the means 2 for setting a white color shielding degree.

Figure 3:
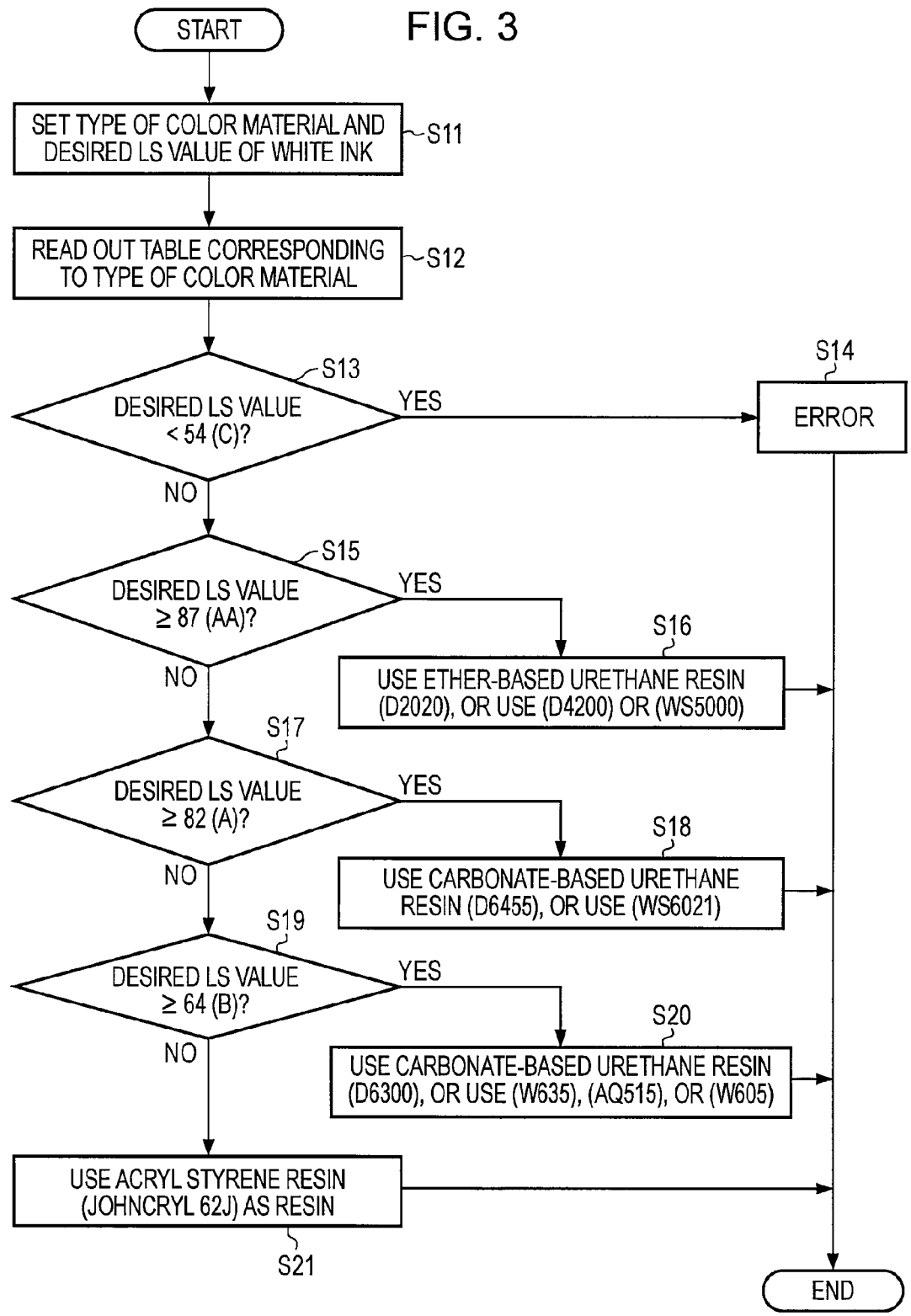
FIG. 3 is s flowchart illustrating detailed operations for determining the type of fixing resin in a method for manufacturing a white ink of the invention.

After the color material and the white color shielding degree are set, in accordance with the set value of the white color shielding degree, the arithmetic processing portion 4 retrieves candidates for the type of fixing resin with reference to the table stored in advance which defines the relationship between the fixing resin corresponding to the color material and the white color shielding degree and works as shown in a flowchart of FIG. 3.

Next, detailed operations of the method for manufacturing an ink of the invention will be described using the flowchart of FIG. 3.

A color material used in a white ink to be manufactured and a desired white color shielding degree (LS value) thereof are set (Step S11). In this step, as the LS value thus set, a desired value may be set, for example, in accordance with an application method of a white color printed material printed with the white ink.

A table corresponding to the color material is read out (Step S12).

It is judged whether the set LS value is less than 54 or not (Step S13).

When the judgment in Step S13 is "Yes", since the LS value is out of the range of the desired white color shielding degree in this method for manufacturing a white ink, the process is finished as "ERROR" (Step S14).

When the judgment in Step S13 is "No", it is judged whether the set LS value is not less than 87 or not (Step S15)

When the judgment in Step S15 is "Yes", in accordance with the color material read out in Step S12, with reference to the table which defines the relationship between the fixing resin and the white color shielding degree, the use of an ether-based urethane resin (D2020) is temporarily determined as the resin (Step S16).

In addition, a blend (D4200) of an ether-based urethane resin and a carbonate-based urethane resin or an ester-based urethane resin (WS5000) may also be used instead, and among those mentioned above, an appropriate resin is finally determined.

When the judgment in Step S15 is "No", it is judged whether the set LS value is not less than 82 or not (Step S17).

When the judgment in Step S17 is "Yes", in accordance with the color material read out in Step S12, with reference to the table which defines the relationship between the fixing resin and the white color shielding degree, the use of a carbonate-based urethane resin (D6455) is temporarily determined as the resin (Step S18).

In addition, an ether-based urethane (WS6021) may also be used instead, and among those mentioned above, an appropriate resin is finally determined.

When the judgment in Step S17 is "No", it is judged whether the set LS value is not less than 64 or not (Step S19).

When the judgment in Step S19 is "Yes", in accordance with the color material read out in Step S12, with reference to the table which defines the relationship between the fixing resin and the white color shielding degree, the use of a carbonate-based urethane resin (D6300) is temporarily determined as the resin (Step S20).

In addition, a carbonate-based urethane (W635), a polyethylene resin (AQ515), and an ester-based urethane resin (W605) may also be used instead, and among those mentioned above, an appropriate resin is finally determined.

Alternatively, when hollow resin particles are also set as the color material, the hollow resin particles as the color material and D6455 (Example 5) as the urethane resin may also be used, among those mentioned above, appropriate materials may be finally determined.

When the judgment in Step S19 is "No", in accordance with the color material read out in Step S12, with reference to the table which defines the relationship between the fixing resin and the white color shielding degree, the use of an acryl styrene resin (Johncryl 62J) is determined as the resin (Step S21).

In addition, in the steps described above, when a plurality of candidates for the white ink composition is present, in order to finally determine the composition among them, a method may be performed in such a way that a plurality of candidates is displayed in a display device of the support apparatus for manufacturing a white ink composition, and a user of the apparatus selects the composition from the candidates thus displayed. Alternatively, other conditions are further input in the apparatus, and in consideration thereof, the composition may be determined. As the other conditions, for example, more detailed conditions of the LS value and/or the names of materials which are now commercially available may be mentioned, and when it is determined that titanium dioxide particles are preferentially used as the color material, for example, an ink composition using titanium dioxide may be input as one of the other conditions.

As the procedure shown in the above flowchart, in accordance with a desired set value of the white color shielding degree, with reference to the table stored in advance which defines the relationship in accordance with the color material between the fixing resin and the white color shielding degree, the type of fixing resin is determined, so that a white ink having a desired white color shielding degree can be obtained.

In the explanation of the above flowchart, the number of levels are 4 stages (AA, A, B, and C), and the threshold values between the levels of the white color shielding degree are set to 54, 64, 82, and 87; however, the values must not be always limited to those mentioned above.

Next, with reference to FIG. 9, the table stored in advance which defines the relationship in accordance with the color material between the fixing resin and the white color shielding degree will be described.

Incidentally, FIG. 8 is a table in which the names of resins and compositions thereof are shown.

FIG. 9 shows one example of the table which defines the relationship among the type of fixing resin, the L* value, the integrated value, the appearance (level), and the white color shielding degree (LS value), which is obtained when titanium dioxide is used as the color material. In the table shown in FIG. 9, there are shown one example rated as a level E, one example rated as a level D, one example rated as a level C, four examples rated as a level B, two examples rated as a level A, three examples rated as a level AA, and one example in which a hollow resin is used as the color material.

When the white color shielding degree of a manufactured white ink is measured, the content of this table can be renewed and further enriched.

Next, representative examples used for forming the contents of Table 9 will be described.

Table 1 of FIG. 4 shows representative examples in which the white color shielding degrees (LS values) are evaluated at the levels AA, A, B, C, D, and E.

FIG. 4 shows examples in which titanium dioxide and a hollow resin are used as the color material (the case in which no color material is used is also included), and in which as the fixing resin, representative acryl styrene resin ("Johncryl 62J" manufactured by BASF), urethane resin A ("D6300" manufactured by Dainichiseika Color & Chemical Mfg. Co., Ltd.), urethane resin B ("D6455" manufactured by Dainichiseika Color & Chemical Mfg. Co., Ltd.), and urethane resin C ("D2020" manufactured by Dainichiseika Color & Chemical Mfg. Co., Ltd.) are used (the case in which no fixing resin is used is also included).

In the examples shown in FIG. 4, according to Reference Example 1 in which no color material and no fixing resin are used (only PET as a recording medium is used), the L* value cannot be measured, and since light is substantially transmitted, the integrated value is 12,136, the LS value is 0, and the shielding degree is evaluated as E.

In Reference Example 2 in which 10 percent by mass of titanium dioxide is used as the color material, no fixing resin is used, and 1 percent by mass of a surfactant, 2 percent by mass of propylene glycol, 5 percent by mass of 1,2-hexanediol, 2 percent by mass of 2-pyrrolidone, and water as the balance are used, the L* value is 70.3, the integrated value is 1,113.9, the LS value is 4.7, and the shielding degree is evaluated as D. In addition, from the results of Reference Example 2, it is found that in the white ink in which although titanium dioxide is used as the color material, no fixing resin is included, the shielding degree is considerably degraded as compared to that of a white ink including a fixing resin.

Hence, in order to obtain a white ink having a high white color shielding degree, a white ink including titanium dioxide and a fixing resin is preferably used.

On the other hand, in Example 1-1 in which 10 percent by mass of titanium dioxide particles is used as the color material, 4 percent by mass of an acryl styrene resin ("Johncryl 62J" manufactured by BASF) is used as the fixing resin, and 1 percent by mass of a surfactant, 2 percent by mass of propylene glycol, 5 percent by mass of 1,2-hexanediol, 2 percent by mass of 2-pyrrolidone, and water as the balance are used, the L* value is 76.8, the integrated value is 194.3, the LS value is 60, and the shielding degree is evaluated as C.

In addition, in Example 2-1 in which 10 percent by mass of titanium dioxide is used as the color material, 4 percent by mass of a urethane resin (A: "D6300" manufactured by Dainichiseika Color & Chemical Mfg. Co., Ltd.) is used as the fixing resin, and 1 percent by mass of a surfactant, 2 percent by mass of propylene glycol, 5 percent by mass of 1,2-hexanediol, 2 percent by mass of 2-pyrrolidone, and water as the balance are used, the L* value is 74.8, the integrated value is 151.76, the LS value is 64, and the shielding degree is evaluated as B.

In addition, in Example 3-1 in which 10 percent by mass of titanium dioxide is used as the color material, 4 percent by mass of a urethane resin (B: "D6455" manufactured by Dainichiseika Color & Chemical Mfg. Co., Ltd.) is used as the fixing resin, and 1 percent by mass of a surfactant, 2 percent by mass of propylene glycol, 5 percent by mass of 1,2-hexanediol, 2 percent by mass of 2-pyrrolidone, and water as the balance are used, the L* value is 75.3, the integrated value is 119.17, the LS value is 86, and the shielding degree is evaluated as A.

In addition, in Example 4-1 in which 10 percent by mass of titanium dioxide is used as the color material, 4 percent by mass of a urethane resin (C: "D2020" manufactured by Dainichiseika Color & Chemical Mfg. Co., Ltd.) is used as the fixing resin, and 1 percent by mass of a surfactant, 2 percent by mass of propylene glycol, 5 percent by mass of 1,2-hexanediol, 2 percent by mass of 2-pyrrolidone, and water as the balance are used, the L* value is 74.9, the integrated value is 102.45, the LS value is 96, and the shielding degree is evaluated as AA.

In addition, in Example 5 in which 10 percent by mass of a hollow resin is used as the color material, 4 percent by mass of a urethane resin (B: "D6455" manufactured by Dainichiseika Color & Chemical Mfg. Co., Ltd.) is used as the fixing resin, and 1 percent by mass of a surfactant, 2 percent by mass of propylene glycol, 5 percent by mass of 1,2-hexanediol, 2 percent by mass of 2-pyrrolidone, and water as the balance are used, the L* value is 78.5, the integrated value is 194.5, the LS value is 69, and the shielding degree is evaluated as B.

From the results shown in Table 4, it is understood that when titanium dioxide is used as the color material, and an urethane resin is used as the fixing resin, although the LS value varies depending on the type of urethane resin, the LS value is superior as a whole.

In addition, it is understood that when hollow resin particles are used as the color material, although the L* value is high, the LS value is not so high as compared to that in the case in which the same urethane resin is used and titanium dioxide is used as the color material.

Next, other examples each having an equivalent level of the shielding degree (evaluation) to that of one of Examples of Table 4 are shown in FIGS. 5, 6, and 7.

In Table 2 shown in FIG. 5, as other examples each having the shielding degree (evaluation) B which is the same as that of Example 2-1 of FIG. 4, Example 2-2, Example 2-3, and Example 2-4 are shown in which 4 percent by mass of W635, AQ515, and W605 are used, respectively, as the fixing resin, and in the above examples, the conditions are the same as those of Example 2-1 except for the type of fixing resin.

In Table 3 shown in FIG. 6, as another example having the shielding degree (evaluation) A which is the same as that of Example 3-1 of FIG. 4, Example 3-2 is shown in which 4 percent by mass of WS6021 is used as the fixing resin, and in the above example, the conditions are the same as those of Example 3-1 except for the type of fixing resin.

In Table 4 shown in FIG. 7, as other examples each having the shielding degree (evaluation) AA which is the same as that of Example 4-1 of FIG. 4, Examples 4-2 and Example 4-3 are shown in which 4 percent by mass of D4200 and WS5000 are used, respectively, as the fixing resin, and in the above examples, the conditions are the same as those of Example 4-1 except for the type of fixing resin.

In the above description, the cases are shown by way of example in which titanium dioxide and a hollow resin are used as the color material, and in which as the fixing resin, the urethane resins shown in Table 7 are used; however, the invention is not always limited to the materials described above.

What is claimed is:

1. A method for obtaining and evaluating a white color shielding degree of a white color printed material comprising:
   measuring an L* value of the white color printed material;
   obtaining an integrated value of transmittance of the white color printed material in a visible light region; and
   obtaining the white color shielding degree from the L* value and the integrated value.

2. The method according to claim 1,
   wherein the integrated value of transmittance is an integrated value of transmittance in a wavelength of 380 to 700 nm.

3. The method according to claim 1,
   wherein the white color printed material is a printed material in which recording is performed on a transparent medium with a white ink, and
   the white color shielding degree (LS value) is represented by [(L* value−α)/integrated value]×1,000, the α being a predetermined value between 60 and 70.

4. The method according to claim 3,
   wherein depending on whether the white color shielding degree (LS value) is not less than a predetermined value or not, the white color shielding degree (LS value) is evaluated at one of levels represented by AA, A, B, C, and D.

5. The method according to claim 3,
   wherein the white ink includes at least a color material and a fixing resin.

6. The method according to claim 5,
   wherein the color material includes titanium dioxide particles or hollow resin particles.

* * * * *